Figure 1:
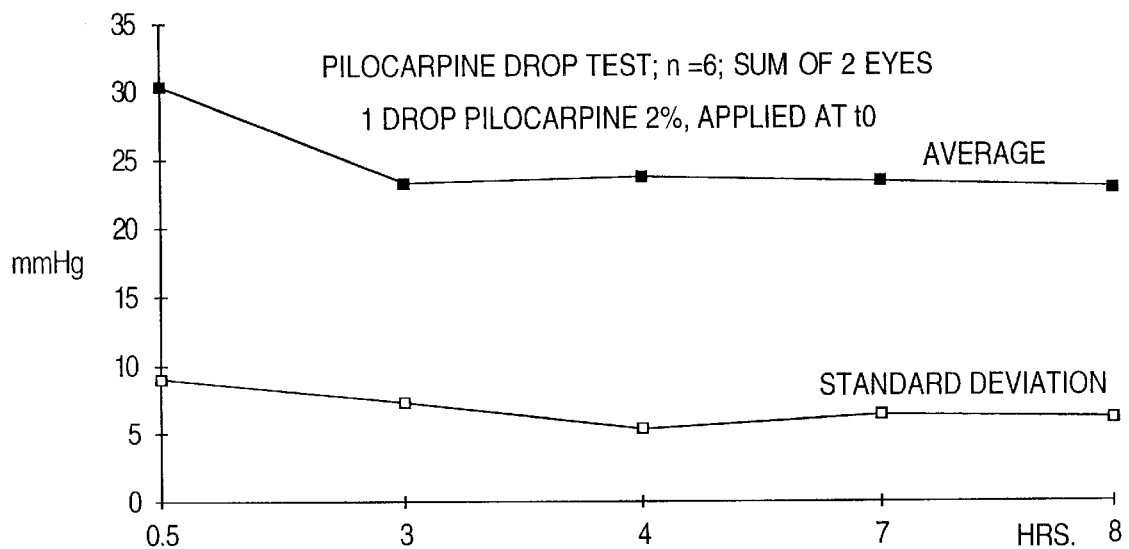

United States Patent

Deurer et al.

Patent Number: 5,869,086
Date of Patent: Feb. 9, 1999

[54] SYSTEMS FOR THE CONTROLLED RELEASE OF PILOCARPINE

[75] Inventors: Lothar Deurer, Kolbenz; Karlheinz Otto, Vallendar; Thomas Hille, Neuwied, all of Germany

[73] Assignee: LTS Lohmann Therapie-Systeme GmbH, Neuwied, Germany

[21] Appl. No.: 553,346
[22] PCT Filed: Apr. 25, 1994
[86] PCT No.: PCT/EP94/01281
§ 371 Date: Mar. 26, 1996
§ 102(e) Date: Mar. 26, 1996
[87] PCT Pub. No.: WO94/25025
PCT Pub. Date: Nov. 10, 1994

[30] Foreign Application Priority Data

Apr. 28, 1993 [DE] Germany .......... 43 13 928.0

[51] Int. Cl.⁶ .......... A61F 13/00; A61L 15/16
[52] U.S. Cl. .......... 424/449; 424/443; 424/446; 424/447; 424/448
[58] Field of Search .......... 424/443, 446, 424/447, 448, 449; 514/772.3; 523/122

[56] References Cited

U.S. PATENT DOCUMENTS

| | | | |
|---|---|---|---|
| 3,220,960 | 11/1965 | Wichterle et al. | 260/2.5 |
| 3,760,805 | 9/1973 | Higuchi | 128/260 |
| 3,797,494 | 3/1974 | Zaffaroni | 128/268 |
| 3,987,790 | 10/1976 | Eckenhoff et al. | 128/260 |
| 4,137,300 | 1/1979 | Sheth et al. | 424/21 |
| 4,144,317 | 3/1979 | Higuchi et al. | 424/21 |
| 4,668,506 | 5/1987 | Bawa | 424/429 |
| 5,008,110 | 4/1991 | Benecke et al. | 424/448 |
| 5,126,144 | 6/1992 | Jaeger et al. | 424/448 |
| 5,254,348 | 10/1993 | Hoffmann et al. | 424/449 |
| 5,273,757 | 12/1993 | Jaeger et al. | 424/448 |
| 5,300,291 | 4/1994 | Sablotsky et al. | 424/78.18 |
| 5,364,629 | 11/1994 | Kochinke et al. | 424/449 |
| 5,474,783 | 12/1995 | Miranda et al. | 424/448 |

FOREIGN PATENT DOCUMENTS

| | | |
|---|---|---|
| 0 219 207 | 4/1987 | European Pat. Off. . |
| 2 163 347 | 2/1986 | United Kingdom . |
| WO 91/01130 | 2/1991 | WIPO . |
| WO93/00058 | 1/1993 | WIPO . |

OTHER PUBLICATIONS

Kuschinsky et al., Kurzes Lehrbuch der Pharmakologie und Toxikologie, 9th edition (George Thieme Verlag. Stuttgart, New York 1981, p. 54.

*Primary Examiner*—Thurman K. Page
*Assistant Examiner*—Kathryne E. Shelborne
*Attorney, Agent, or Firm*—Wenderoth, Lind & Ponack, L.L.P.

[57] ABSTRACT

A transdermal therapeutic system for the controlled active substance release to the skin having a backing layer and a pressure sensitive adhesive reservoir layer, wherein the reservoir layer comprises a polymeric material, a plasticizer, and pilocarpine base or one of the pharmaceutically acceptable salts thereof. Furthermore, the use of a capsule made of a semipermeable membrane for the controlled release of pilocarpine, the capsule comprising the pilocarpine in encapsulated form and having an aperture in the capsular material, for the treatment of glaucoma.

17 Claims, 1 Drawing Sheet

SYSTEMS FOR THE CONTROLLED RELEASE OF PILOCARPINE

The present invention relates to a transdermal therapeutic system for the controlled pilocarpine release to the skin having a backing layer and a pressure sensitive adhesive reservoir layer, to a process for the production of this system, and to the use of a capsule made of a semipermeable membrane for the controlled release of pilocarpine ((3S, 4R)-3-ethyl-4,5-dihydro-4-(1-methyl-1H-imidazole-5-ylmethyl)-2(3H)-furanone).

Pilocarpine is an alkaloid which is recovered from different kinds of the genus pilocarpus (Rutaceae (Rutales)), e.g., Pilocarpus Jaborandi Holmes etc., and has been used in ophthalmology for more than 100 years. Pilocarpine drops are used by patients suffering from glaucoma; they have to be instilled into the conjunctival sac several times a day. In glaucoma there is an increased intraocular pressure which may result in damages of the retina and the optic nerve if left untreated. If applied to the eye, pilocarpine causes a contraction of the pupil, the outflow of the aqueous humor in the eye is facilitated and thus the intraocular pressure reduced. One application persists for 4 to 6 hours so that several applications per day are required to lower the intraocular pressure throughout the day. For this reason an uncontrolled increase in the pressure values particularly occurs in the early morning due to the subsiding action of the dosage instilled in the evening and because of the fact that the intraocular pressure physiologically increases at this time of the day.

Another disadvantage of this form of application is the fact that older patients, who mainly suffer from glaucoma, find it difficult to instil the eye drops and that—due to the repeated instillation—the patients are reminded of their complaints several times a day and cannot dissociate themselves from their disease, resulting in mental strain. Moreover, it is disadvantageous that pilocarpine eye drops—immediately after their administration—result in difficulties in focussing accompanied by impairment of vision.

This problem led to the development of a system similar to contact lenses and containing pilocarpine, described in U.S. Pat. No. 4,144,317. This system known under the trade name Ocusert® was worn in the conjunctival sac for seven days. Although it met all requirements, there were cases where Ocusert® got out of place within the conjunctival sac and could hardly be removed, therefore the drug had to be withdrawn from the market.

Accordingly, there is a demand for pharmaceutical products lowering the intraocular pressure without applying pilocarpine directly to the eye.

Accordingly, it is the object of the present invention to provide a pharmaceutical product for the systemic release of pilocarpine for lowering the intraocular pressure while simultaneously suppressing the side effects.

The above object is achieved by a transdermal therapeutic system according to the invention and by the semipermeable capsule according to the invention. Particularly preferred embodiments of the present invention and to a process for the production of the transdermal therapeutic system are disclased.

The present invention relates to a transdermal therapeutic system having a backing layer and a pressure sensitive adhesive reservoir layer for the controlled active substance release to the skin; the system is characterized by the fact that the reservoir layer comprises a polymeric material, a plasticizer, and a pilocarpine base or one of its pharmaceutically acceptable salts.

Furthermore, the present invention relates to using a capsule made of a semipermeable membrane for the controlled release of pilocarpine, which comprises pilocarpine in encapsulated form and has an aperture in the capsular material, for the treatment of glaucoma.

This solution is surprising all the more, since it is accepted that only extremely high pilocarpine doses—if at all—are suitable to lower the intraocular pressure if the drug is not applied locally, i.e., as eye drops or ointments, or as ocular system, but is administered systemically. Because of its effect on the heart, high doses of pilocarpine are hazardous to patients' life and health.

For example, a specialized publication of the German Federal Board of Health reported on pilocarpine on Nov. 28, 1991:

"If pilocarpine is applied systemically, risks are likely to arise already at a dosage of below 20 mg (single maximum dose for adults)." (loc. cit., page 2) A recognized pharmacological textbook is even more distinct:

"Pilocarpine. This alkaloid from the leaves (Folia Jaborandi) of Pilocarpus pennatifolius specifically stimulates the postganglionic, parasympathetic acetylcholine receptors. In principle it acts as carbachol; however, impairment of the heart function is more distinct. Thus, a general application of pilocarpine is out of question; only local application to the eye can be recommended."

(Kuschinsky, G., Lüllmann, H., Peters, T., Kurzes Lehrbuch der Pharmakologie and Toxikologie, 9th edition (Georg Thieme Verlag Stuttgart New York 1981, page 54).

The doctrine that it is impossible to reduce the intraocular pressure by means of systemically administered pilocarpine without the specific side effects of pilocarpine occurring, is the reason for the absence of a successful clinical investigation publishing the systemic application of pilocarpine to treat the glaucoma—although application forms releasing active substances in a controlled manner are known in the state of the art. The administration of pharmaceutically effective compounds by means of such formulations can be effected orally, transdermally, or otherwise parenterally. In these drugs, pilocarpine may be present as such or in the form of pharmaceutically acceptable acid addition salts, e.g., as hydrohalides, in particular hydrochloride, or as a salt of another pharmaceutically acceptable acid, preferably of nitric acid.

Additionally, these agents generally comprise adjuvants, such as carriers, free-flow agents, solvents and oils, the kind and amount of which varying in accordance with the form of administration. In general, the content of active substance, calculated as free pilocarpine base, amounts to between 0.1–50%-wt., preferably between 2 and 15%-wt.

Some formulations for the oral administration suitable within the present invention are briefly described in the following.

In one formulation, the pharmaceutical active substance is encapsulated, for example, in a semipermeable membrane, e.g. in cellulose acetate. A tiny hole is bored into the capsular material by means of a piercer or laser. Within the body of the treated patient water is absorbed through the capsular material. The pharmaceutical active substance is forced through the tiny aperture in the desired gradual, constant and controlled manner by osmotic pressure. Such systems are described, e.g., in U.S. Pat. Nos. 3,760,805 and 3,987,790. The pharmaceutical active substances may be present in these systems in solid form or absorbed to ion-exchange resins.

Another system for oral administration is described by Sheth and Leeson in U.S. Pat. No. 4,137,300. This patent describes a formulation comprising a wax matrix.

The active substances of the present invention are administered by means of adequate formulations in a convenient and suitable manner. The solid active substances may be administered in solution or as suspension.

The solution or suspension medium may be an aqueous or organic one. Suitable solution or suspension media for pilocarpine include, for example, water, silicone fluid or mineral oil.

In order to facilitate the administration of a compound by means of a formulation as described above, a free-flow agent may be added to the system. Some suitable free-flow agents for oral formulations, for example, include polyethylene glycol, hydroxypropyl methyl cellulose and sugar.

The best embodiment of a drug for the controlled systemic administration of pilocarpine to treat glaucoma is the transdermal therapeutic system (TTS). Based on theoretical considerations, the passage of pilocarpine through the skin should be good, and there are many patents describing the transdermal route for pilocarpine as being possible; however, the teachings of these patents do not indicate the manner glaucoma can be treated with a pilocarpine-containing TTS, and there is no pilocarpine-TTS available on the market so far.

For example, a TTS may consist of a backing layer, a pressure sensitive adhesive reservoir layer containing the active substance, and a removable protective layer. Preferably, the backing layer is impermeable to active substances.

The backing layer which is impermeable to active substances may consist of flexible or inflexible material.

Substances suitable for its production include polymer films or foils, such as an aluminum foil, which are used alone or coated with a polymeric substrate.

Textile fabrics may also be used, provided that the components of the reservoir—owing to their physical nature—may not pass through. According to a preferred embodiment, the backing layer is a composite of an aluminized sheet.

The reservoir layer consists of a polymeric material and the active substance, with the polymeric material ensuring the cohesion of the system. It comprises a base polymer and, optionally, conventional additives. The selection of the base polymer depends on the chemical and physical properties of the pilocarpine. Examples of such polymers include rubber, rubber-like synthetic homopolymers, copolymers, block polymers, block copolymers, polyacrylic acid esters and the copolymers thereof, polyurethanes, silicones, and polyacrylates. In principle, all polymers are suitable which may be used in the production of pressure sensitive adhesives and which are physiologically acceptable. Particularly preferred ones are those consisting of block copolymers based on styrene and 1,3-dienes, polyisobutylenes, silicones, polymers based on acrylate and/or methacrylate.

Among the block copolymers based on styrene and 1,3-dienes linear styrene-isoprene or styrene-butadiene-block copolymers are particularly used.

Preferred polymers based on acrylate include self-crosslinking acrylate copolymers of 2-ethyl hexyl acrylate, vinyl acetate, and acrylic acid, or non-self-crosslinking acrylate copolymers with or without chelate esters.

According to a preferred embodiment of the present invention the polymer material, selected from the group of polyacrylates, is a polymerization product of acrylic acid and its esters, or methacrylic acid and its esters. Preferably, the esters of acrylic acid comprise as alcohol components alcohols having 2–4 carbons. According to a preferred embodiment, the esters of acrylic acid comprise as alcohol component straight-chain or branched alcohols having 4–10 carbons. Additionally, the esters of the methacrylic acid may comprise as alcohol components amino alcohols.

Suitable polymers which are added to the basic polymer include polymethacrylates and polyvinyls.

Preferred methacrylates include copolymers based on dimethylaminoethyl methacrylates and neutral methacrylic esters.

Polyvinyl pyrrolidines and polyvinyl alcohols are preferably used as polyvinyls.

The selection of the plasticizer depends on the polymer. Particularly suitable are higher alcohols, such as dodecanol, undecanol, octanol, oleyl alcohol and 2-octyl dodecanol, as well as esters of carboxylic acids (e.g., isopropyl myristate or isopropyl palmitate, wherein the alcohol component may also be a polyethoxylated alcohol; diesters of dicarboxylic acids, e.g., di-n-butyladipate, as well as triglycerides, in particular medium-chain triglycerides of the caprylic/capric acids of coconut oil). Additional examples of a suitable plasticizer include polyfunctional alcohols, e.g. glycerol and 1,2-propanediol and others, these may be etherified by polyethylene glycols.

Suitable penetration enhancers include all carboxylic acids which are physiologically acceptable. Particularly suitable are octanoic acid, laevulinic acid, undecenoic acid, oleic acid, as well as stearic acid and their isomers.

The nature of the conventional additives depends on the polymer used. According to their function they may be classified, e.g., into tackifiers, stabilizers, carriers, and fillers. The suitable physiologically acceptable substances are known to those skilled in the art.

The self-tackiness of the reservoir layer is strong enough to ensure permanent contact to the skin.

The removable protective layer which is in contact with the reservoir layer and is removed prior to use, for example, consists of the same materials as those used for the manufacture of the backing layer, provided that they are rendered removable, e.g., by a silicone treatment. Other removable protective layers, for example, are polytetrafluoroethylene, treated paper, cellophane, polyvinyl chloride, and the like. If the laminate according to the present invention is cut into sizes (patches) corresponding to the therapeutic purpose prior to applying the protective layer, the formats of the protective layer then to be applied may have a projecting end, facilitating its removal from the patch.

According to an embodiment of the present invention the reservoir layer comprises 40–85%-wt. of polymeric material, 0–30%-wt. of plasticizer, and 0.1–30%-wt. of pilocarpine base or one of its pharmaceutically acceptable salts. Preferably, the reservoir layer has 40–80%-wt. of polymeric material, 0–30%-wt. of plasticizer, and 0.1–30%-wt. of pilocarpine base.

The process for the production of a transdermal therapeutic system comprises dissolving self-crosslinking acrylate copolymer in a mixture of organic solvents, adding a plasticizer and a pilocarpine base, sprinkling polymethacrylates as copolymers, and applying the adhesive solution on an aluminized and siliconized polyester sheet as backing layer, after the polymethacrylates sprinkled therein have been dissolved.

The transdermal therapeutic system according to the present invention is manufactured by homogeneously mixing the active substance together with the components of the pressure sensitive adhesive reservoir layer, optionally in solution, and spreading it onto the backing layer which is impermeable to the active substance, followed by removal of the solvent(s), if necessary. Subsequently, the adhesive layer is provided with an adequate protective layer.

In principle the reverse is also possible, i.e., that the adhesive solution is spread on the protective layer. In this case too, the solvents are removed and the backing layer is applied.

The invention will be illustrated by the following examples:

Example 1

0.351 kg isopropyl myristate and 0.468 kg pilocarpine base are added under stirring to 7.47 kg of a 42.3% self-crosslinking solution of pressure sensitive adhesive (acrylate copolymer based on 2-ethyl hexyl acrylate, vinyl acetate, and acrylic acid, dissolved in a mixture of ethyl acetate, heptane, ethanol, and methanol). Subsequently, 0.702 kg of a copolymer based on dimethylaminoethyl methacrylate and neutral methacrylic ester are sprinkled into the mixture. Stirring at room temperature is continued until the solids are completely dissolved. The evaporation loss is compensated. 8.991 kg 52.0% (w/w) active substance-containing adhesive solution result which is spread on an aluminized and siliconized polyester sheet by means of a 350 µm coating knife. After the solvents have been removed by drying, the adhesive film is covered with a polyester sheet having a thickness of 15 µm. An area of 25 cm² is punched by means of suitable cutting tools, and the edges are separated off. The release relating to both this and the other examples is listed in the table; the list indicates both the controlled release into a physiological saline and through excized rodent skin.

All further examples are carried out in accordance with the procedure of Example 1. The liquid components are always mixed first, then methacrylate copolymer based on dimethylaminoethyl methacrylate and neutral methacrylic esters is added. The following table indicates the formulation components after drying. The abbreviations have the following meanings:

neutral PA: acrylate copolymer of 2-ethyl hexyl acrylate, vinyl acetate, and acrylic acid, A.V.<1
acidic acrylate: acrylate copolymer of 2-ethyl-hexyl acrylate, vinyl acetate, and acrylic acid, A.V.≅40
PMA: copolymer with basic character, based on dimethylaminoethyl methacrylate and neutral methacrylic esters
IPM: isopropyl myristate The in-vitro-release was determined in a shaking water bath at 37° C. The acceptor medium was 100 ml physiological saline which was completely changed after 2, 4 and 8 hours. The concentration was determined by HPLC after 2, 4, 8 and 24 hours. The penetration through mice skin was measured by means of Franz' diffusion cells.

In order to test the efficacy of the pilocarpine-TTS clinically, a first clinical trial of the TTS (Example 1) was carried out in comparison to 2% eye drops with 6 healthy test persons. The test was carried out with healthy individuals, since, on the one hand, there is no data with respect to the therapeutic efficacy in case of an already existing glaucoma and to the transdermal application of pilocarpine but, on the other hand, it is known that the intraocular pressure can be lowered by pilocarpine even in healthy individuals.

Owing to the unknown therapeutic efficiency of transdermally applied pilocarpine the application to patients suffering from glaucoma was out of question first. Since the effect of reducing the intraocular pressure by means of pilocarpine in the healthy eye is considerably lower than in an eye of a glaucoma patient, the test persons were treated not only with the TTS but also with eye drops in order to allow a direct comparison of both administration forms. To exclude the possibility that residues of pilocarpine in the eye are responsible for lowering the intraocular pressure, one week passed between the application of the eye drops and that of the TTS.

TABLE 1

Pilocarpine release from different pilocarpine TTS

| Example | Pilocarpine base | PA | PMA | Plasticizer | Liberation pil. [mg/25 cm² × 24 h] | Pentetration pil. [mg/ cm² × 24 h] |
|---|---|---|---|---|---|---|
| 1 | 10% | neutr.PA 67.50% | 15% | 7.5% IPM | 28 mg | 1.1 mg |
| 2 | 10% | neutr.PA 67.50% | 15% | 7.5% oleyl alcohol | 20 mg | 0.7 mg |
| 3 | 10% | neutr.PA 67.50% | 15% | 7.5% 1-dodecanol | 13 mg | 0.9 mg |
| 4 | 10% | acidic PA 62.50% | 20% | 7.5% IPM | 23 mg | 0.7 mg |
| 5 | 10% | acidic PA 62.50% | 20% | 7.5% oleyl alcohol | 25 mg | 1.1 mg |

THE BRIEF DESCRIPTION OF THE DRAWINGS

Figure 2:
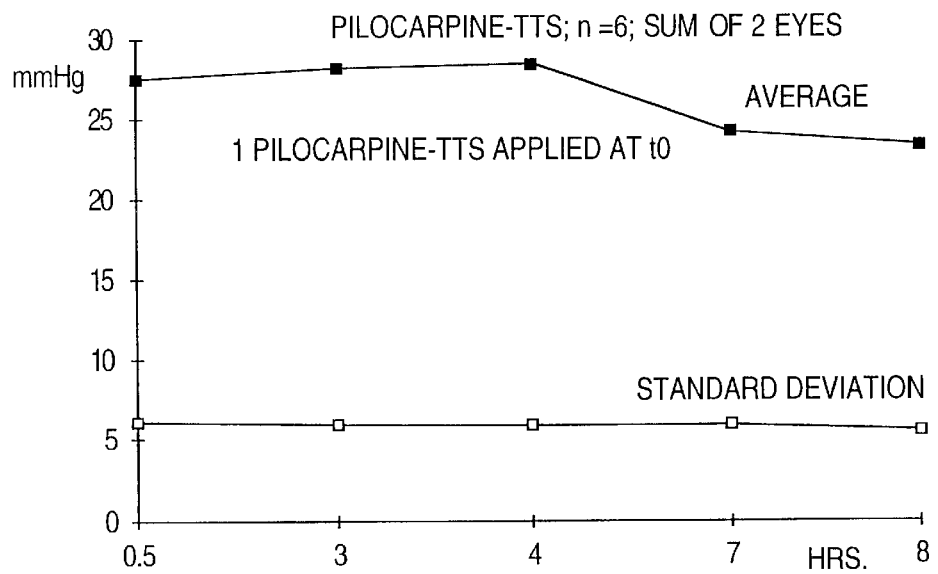

The action of pilocarpine after intraocular and transdermal administration is shown in FIGS. 1 and 2.

The graphs in FIGS. 1 and 2 result from representing the measured average values of n=6 test persons versus time. Since the pressure reduction is effected by a systemic effect in the case of the TTS, no difference was made between left and right eye, the sum of both eye pressures was taken into consideration instead.

In order to compare the effects of drops and TTS directly, this form of evaluation was also chosen for the drops. The measurements of the intraocular pressure were carried out automatically and without contact, during wearing the pilocarpine TTS for 8 hours, and up to 8 hours after instillation of pilocarpine eye drops, respectively. The examinations were carried out by an ophthalmologist using a computer tonometer (CT 20 D, by Top-con).

It can be seen that applying both administration forms to eyes of healthy individuals only results in a slight pressure change (sum pressure change of both eyes 5 mm and 6 mm Hg, respectively). However, it can also be seen that the effects of both administration forms are of the same order, a fact that could not be expected in view of the latest level of knowledge and which is surprising all the more, since there were no pilocarpine-specific side effects during the TTS application.

It is remarkable that, although the reduction of the intraocular pressure by means of the TTS is of the same order as that of the eye drops, it starts considerably later. This phenomenon can be explained by the normal function mode of a TTS, since the plasma levels after administration via the transdermal route build up not until after a certain period of time, the so-called "lag time".

The results shown in FIGS. 1 and 2 demonstrate that—in contrast to the conventional doctrines—it is possible to reduce the intraocular pressure by means of systemically administered pilocarpine, without having to accept the side effects of pilocarpine, provided that the administration of pilocarpine is effected in a controlled manner.

We claim:

1. A transdermal therapeutic system for lowering the intraocular pressure of a patient in a controlled manner without direct application to the eye, through systemic active substance release to the skin, said system having an active substance-impermeable backing layer, a pressure-sensitive adhesive reservoir layer and a removable protective layer, wherein the reservoir layer comprises (1) 40–85 wt. % of a polymeric material selected from the group consisting of rubber, synthetic rubber, polyacrylic acid esters and the copolymers thereof, polyurethanes, silicones and polyacrylates, (2) 0.1–30 wt. % of a pilocarpine base or a pharmaceutically acceptable salt thereof, and (3) at least one plasticizer in an amount of up to 30 wt. %.

2. A transdermal therapeutic system according to claim 1 wherein the polymeric material consists of block copolymers based on styrene and 1,3-dienes, polyisobutylenes, silicones, polymers based on acrylate and/or methacrylate.

3. A transdermal therapeutic system according to claim 2, wherein the block copolymers based on styrene and 1,3-dienes are linear styrene-isoprene or styrene-butadiene block copolymers.

4. A transdermal therapeutic system according to claim 1, wherein the polymeric material comprises self-crosslinking acrylate copolymers.

5. A transdermal therapeutic system according to claim 1, wherein the polymeric material comprises non-self-crosslinking acrylate copolymers.

6. A transdermal therapeutic system according to claim 4, wherein the polymeric material comprises self-crosslinking acrylate copolymers having chelating agents.

7. A transdermal therapeutic system according to claim 5, wherein the polymeric material comprises non-self-crosslinking acrylate copolymers having chelating agents.

8. A transdermal therapeutic system according to claim 1, wherein the polymeric material, is a polymerization product of acrylic acid and the esters thereof or of methacrylic acid and the esters thereof.

9. A transdermal therapeutic system according to claim 8, wherein the esters of the acrylic acid comprise, as alcohol components, alcohols having 2–4 carbons.

10. A transdermal therapeutic system according to claim 8, wherein the esters of the acrylic acid comprise, as alcohol components, straight-chain or branched alcohols having 4–10 carbons.

11. A transdermal therapeutic system according to claim 8, wherein the esters of the methacrylic acid comprise, as alcohol components, amino alcohols.

12. A transdermal therapeutic system according to claim 1, wherein polymers, which are selected from polymethacrylates and polyvinyls, are added to the base polymer.

13. A transdermal therapeutic system according to claim 1, wherein the reservoir layer comprises 40–80%-wt. of polymeric material, 0–30%-wt. of plasticizer, and 0.1–30%-wt. of pilocarpine base or a pharmaceutically acceptable salt thereof.

14. A process for the production of a transdermal therapeutic system according to claim 1, comprising: dissolving a self-crosslinking acrylate copolymer in a mixture of organic solvents, adding a plasticizer and pilocarpine base or a pharmaceutically acceptable salt thereof, sprinkling polymethacrylates as copolymers, and applying the adhesive solution to an aluminized and siliconized polyester sheet as backing layer, after dissolution of the polymethacrylates sprinkled therein.

15. A transdermal therapeutic system according to claim 1 for the treatment of glaucoma.

16. A transdermal therapeutic system according to claim 15, wherein the controlled active substance release is effected in order to avoid or to minimize the side effects of pilocarpine.

17. A method for the treatment of glaucoma which comprises applying to the skin of a patient in need of such treatment a transdermal therapeutic system as defined in claim 1.

* * * * *